United States Patent

Bovendeur et al.

[11] Patent Number: 5,203,212
[45] Date of Patent: Apr. 20, 1993

[54] METHOD FOR DETERMINING THE COMPOSITION OF A SAMPLE

[75] Inventors: Jan Bovendeur, Renkum; Barend J. Visser, Ar Veen, both of Netherlands

[73] Assignee: Serasea B.V., Waalwijk, Netherlands

[21] Appl. No.: 654,310

[22] Filed: Feb. 12, 1991

[30] Foreign Application Priority Data

Feb. 13, 1990 [NL] Netherlands ............ 9000341

[51] Int. Cl.$^5$ .............................................. G01L 5/24
[52] U.S. Cl. ................................................ 73/863.21
[58] Field of Search ............... 73/863.21, 863.41, 866, 73/28.06

[56] References Cited

U.S. PATENT DOCUMENTS

| 2,353,828 | 7/1944 | Hyde ...................... 73/863.21 |
| 2,947,164 | 8/1960 | Orr, Jr. .................... 73/28.06 |
| 4,135,388 | 1/1979 | Orr, Jr. . |
| 4,479,379 | 10/1984 | Tarcy ...................... 73/863.21 |

FOREIGN PATENT DOCUMENTS

| 0178009 | 4/1986 | European Pat. Off. . |
| 0313116 | 4/1989 | European Pat. Off. . |
| 1550358 | 3/1990 | U.S.S.R. ................. 73/863.21 |

Primary Examiner—Robert Raevis
Attorney, Agent, or Firm—Webb, Burden, Ziesenheim & Webb

[57] ABSTRACT

Method for determining the composition of a sample of for example dredging sludge by separating the sample into fractions, analyzing the fractions geophysically and/or physical-chemically and by further characterizing the fractions wherein the sample is separated in accordance with a preselected pattern of weight-criteria.

17 Claims, 1 Drawing Sheet

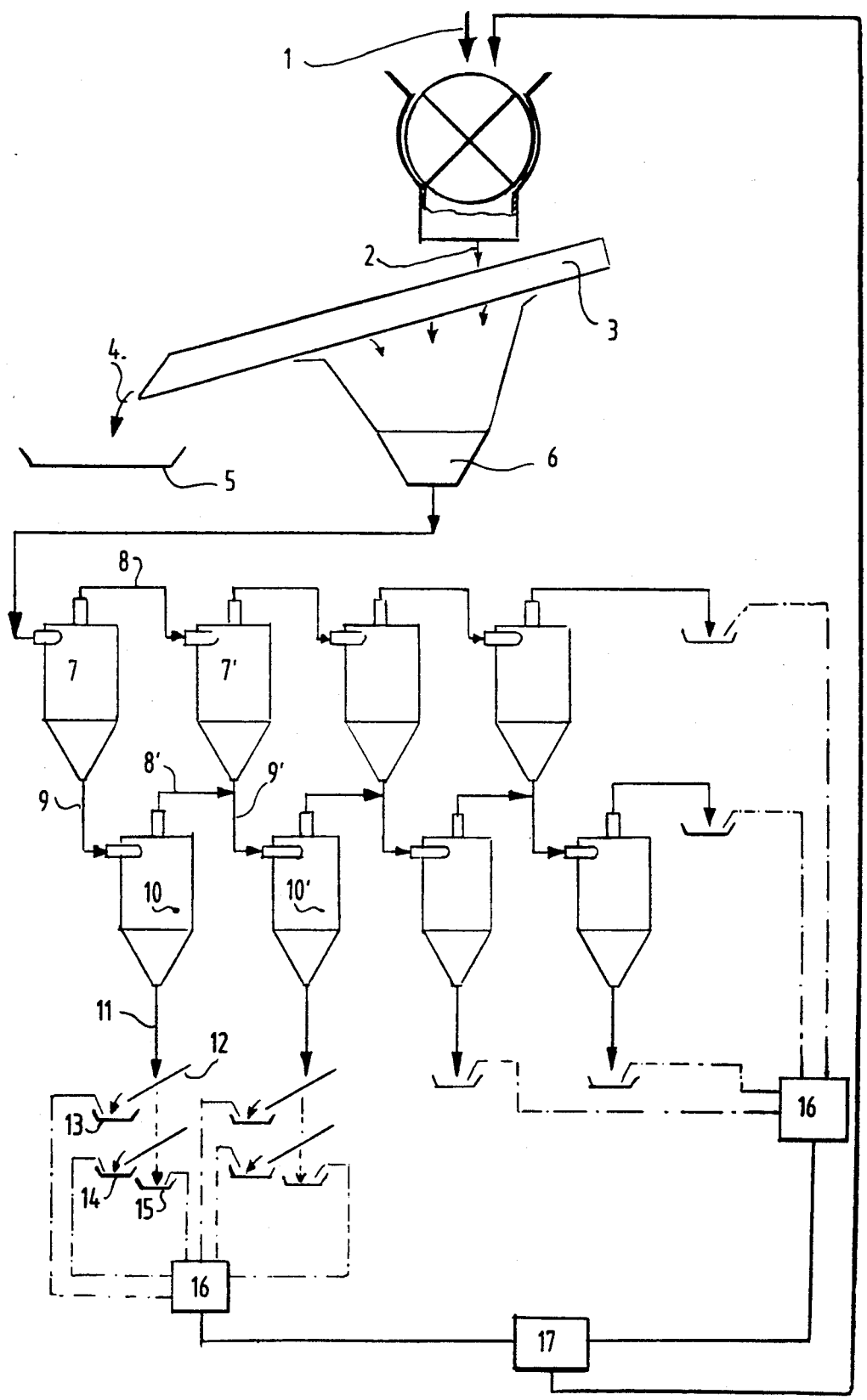

METHOD FOR DETERMINING THE COMPOSITION OF A SAMPLE

The invention relates to a method for determining the composition of a sample, for example of dredging sludge, by separating the sample into fractions, subsequently analyzing it geophysically and/or physical-chemically and by further characterizing the fractions.

There are large amounts of polluted ground material possibilities for responsible storage of this material are, however, insufficient. The polluted material is therefore separated by means of splitting the material into fractions. The separation can on the one hand take place into pollutant/polluted material and non-polluted material. On the other hand, when the whole of the material is polluted, separation can take place into a cleanable and a non-cleanable fraction. The volume of the polluted fractions as well as that of the non-cleanable fractions will be smaller than the total volume. In order to obtain a good separation between clean, i.e. non-polluted or cleanable, and non-clean, i.e. polluted or non-cleanable, volume, an attempt is made on the basis of the distribution of the pollution to arrive at a corresponding fraction distribution. In order to gain an insight into the distribution of the pollution, the composition of the ground sample will first have to be determined. This takes place by means of fraction separation and subsequent geophysical and/or physical-chemical analysis and further characterizing of the fractions. On the basis hereof can be determined the ultimate fraction distribution that will be applied in practice.

In known methods for assessing the composition of a ground sample the separation into fractions takes place on the basis of differences in grain size, while in practice the bulk separation is based on weight differences between the grains. These varying approaches have the drawback that the fraction pattern after bulk separation varies considerably from the pattern expected as a result of the determining of the composition. The consequence hereof is that in practice the separation into fractions is not optimal, whereby it can occur either that not all of the pollution is isolated or that the polluted fraction contains a large portion of non-polluted material, whereby the volume is unnecessarily enlarged.

The object of the invention is to provide a method for determining the composition of ground samples which better approximates the situation in practice and prevents the above described drawbacks. This is achieved according to the invention in that the composition is determined by separating the sample in accordance with a selected pattern of weight criteria.

The fraction distribution can further be optimalized in that the pattern of weight criteria is re-selected on the basis of the results of the geophysical and/or physical-chemical analysis and further characterizing, and the method then repeated. Used for the first separation of the ground sample into fractions is a pattern of weight criteria based on the distribution of the pollution to be anticipated in the light of the known history. In the case for instance of the expected presence of heavy metals in the ground sample, the pattern of weight criteria can be based on the weights of particular ground particles having heavy metals bonded thereto.

The FIGURE gives a schematic view of an embodiment of the method according to the present invention.

A portion 2 of the ground sample 1 is rid by means of a sieve 3 of comparatively large particles 4 which are collected in a tray 5. A number of hydrocycloning steps are performed with the remaining material 6, wherein the number of steps is dependent on the selected pattern of weight criteria.

At each hydrocyclone step the particles with a specific gravity greater than or equal to the weight criterion associated with that step are separated from the residue 8 by means of one of the primary hydrocyclones 7. The thus separated fraction 9, the so-called underflow, is carried through one of the secondary hydrocyclones 10. The underflow 11 of this cyclone can optionally be further fractionated by means of a rocking table 12. The fractions 13, 14, 15 herein formed are then chemically analyzed 16.

The material remaining after the first primary hydrocyclone 7, namely the residue 8, is carried through the following primary hydrocyclone 7'. The residue 8' from the secondary cyclone 10 is carried together with the underflow 9' to one of these following secondary hydrocyclones 10'.

After the chemical analysis 16, it may be decided in the light of the results 17 of this analysis to repeat the whole procedure with a modified pattern of weight criteria. By means of one or more repetitions an optimal fraction distribution, that is, with the smallest possible number of polluted fractions or the best possible separation between cleanable and non-cleanable fractions, can eventually be obtained that can be applied in practice.

We claim:

1. A method for determining the composition of a sample by separating the sample into fractions, subsequently analyzing said sample geophysically and/or physical-chemically and by further characterizing the fractions, characterized in that the composition is determined by separating the sample in accordance with a first selected pattern of weight criteria; wherein said sample is of dredging sludge.

2. Method as claimed in claim 1, characterized in that the pattern of weight criteria is re-selected on the basis of the results of the geophysical and/or physical-chemical analysis and further characterizing and the method according to claim 1 is then repeated.

3. Method as claimed in claim 2, characterized in that for separation into fractions the sample is carried through a hydrocyclone and the fractions obtained therefrom are separated by means of a rocking table.

4. Method as claimed in claim 1, characterized in that said first selected pattern of weight criteria is based on the anticipated composition of said sample.

5. A method for determining the composition of a sample by separating the sample into fractions, subsequently analyzing said sample geophysically and/or physical-chemically and by further characterizing the fractions, characterized in that the composition is determined by separating the sample in accordance with a first selected pattern of weight criteria; wherein for separation into fractions the sample is carried through a hydrocyclone and the fractions obtained therefrom are separated by means of a rocking table.

6. A method for determining the composition of a sample comprising the steps of:

a) passing said sample through at least one of hydrocycloning steps, the number of hydrocycloning steps is determined by a preselected pattern of weight criteria, wherein said pattern of weight criteria is based on the expected distribution of pollutants in said sample, each said hydrocycloning step includes separation of a separated fraction from a residue of said sample within a primary hydrocyclone, wherein said separated fraction is made up of particles of said sample with a specific gravity greater than or equal to a specific weight criterion associated with that hydrocycloning step, separation of said separated fraction into an underflow and a secondary residue in a secondary hydrocyclone;

b) separating said underflow of said hydrocycloning steps into fractions; and c) analyzing said fractions.

7. The method of claim 6, wherein said sample is of a dredging sludge.

8. The method of claim 6, further comprising the steps of:

d) modifying said pattern of weight criterion according to said analysis; and e) repeating steps a) to d) with said modified pattern of weight criterion until an desired fraction distribution is obtained.

9. The method of claim 8, wherein each said hydrocycloning step further includes separating said residue into a second separated fraction and a third residue in a second primary hydrocyclone;

combining said second separated fraction with said secondary residue; and separating said combined second separated fraction and said secondary residue into a second underflow and a fourth residue in a second secondary hydrocyclone.

10. The method of claim 9, wherein said separating of said underflow is performed by rocking tables.

11. The method of claim 10, wherein said sample is of a dredging sludge.

12. The method of claim 6, wherein each said hydrocycloning step further includes separating said residue into a second separated fraction and a third residue in a second primary hydrocyclone;

combining said second separated fraction with said secondary residue; and separating said combined second separated fraction and said secondary residue into a second underflow and a fourth residue in a second secondary hydrocyclone.

13. The method of claim 6, wherein said separating of said underflow is performed by rocking tables.

14. The method of claim 6, wherein said analysis of said fractions is a chemical analysis.

15. The method of claim 6, wherein said analysis of said fractions is a geophysical analysis.

16. The method of claim 6, wherein said analysis of said fractions includes a geophysical analysis of said fractions and a chemical analysis of said fractions.

17. The method of claim 6, further comprising the step of passing said sample through a sieve to remove relatively large particles from said sample prior to said hydrocycloning steps.

* * * * *